(12) United States Patent
Nigola et al.

(10) Patent No.: US 9,162,077 B2
(45) Date of Patent: Oct. 20, 2015

(54) WIDE SPECTRUM LED COMPONENTS

(75) Inventors: Annemari Nigola, Hong Kong (HK); Yue-Chi Lai, Hong Kong (HK); Juha Rantala, Hong Kong (HK)

(73) Assignee: Lumichip Limited, Hong Kong (HK)

( * ) Notice: Subject to any disclaimer, the term of this patent is extended or adjusted under 35 U.S.C. 154(b) by 0 days.

(21) Appl. No.: 14/005,827

(22) PCT Filed: Mar. 19, 2012

(86) PCT No.: PCT/FI2012/050259
§ 371 (c)(1),
(2), (4) Date: Mar. 25, 2014

(87) PCT Pub. No.: WO2012/127107
PCT Pub. Date: Sep. 27, 2012

(65) Prior Publication Data
US 2014/0248678 A1    Sep. 4, 2014

Related U.S. Application Data

(60) Provisional application No. 61/453,984, filed on Mar. 18, 2011.

(30) Foreign Application Priority Data

Mar. 18, 2011 (FI) .................................... 20115268

(51) Int. Cl.
*A61N 5/06* (2006.01)
*H01L 33/52* (2010.01)
(Continued)

(52) U.S. Cl.
CPC .............. *A61N 5/0613* (2013.01); *A01G 7/045* (2013.01); *A61N 5/06* (2013.01); *H01L 25/0753* (2013.01); *H01L 33/50* (2013.01); *H01L 33/502* (2013.01); *H01L 33/52* (2013.01); *A61N 2005/0651* (2013.01); *A61N 2005/0652* (2013.01); *A61N 2005/0659* (2013.01); *A61N 2005/0663* (2013.01); *H01L 2224/45147* (2013.01);
(Continued)

(58) Field of Classification Search
CPC .......... F21Y 2101/02; F21Y 2113/007; H01L 25/0753; H01L 33/504; F21K 9/00
USPC .................................. 362/373, 249, 345, 267
See application file for complete search history.

(56) References Cited

U.S. PATENT DOCUMENTS

2004/0256626 A1    12/2004  Wang et al.
2005/0274959 A1*   12/2005  Kim et al. ........................ 257/79
(Continued)

FOREIGN PATENT DOCUMENTS

EP        1160883 A2       12/2001
WO    WO 2010023840 A1     3/2010

OTHER PUBLICATIONS

Kitabayashi, H., Development of High Power Infrared LED, SEI Technical Review, No. 70, Apr. 2010.

*Primary Examiner* — Tracie Y Green
(74) *Attorney, Agent, or Firm* — Seppo Laine Oy (57) ABSTRACT

An LED component and the use thereof. The component comprises a light output spectrum with at least one peak intensity between 600-800 nm wavelength range with a full width at half maximum at least 50 nm; second optional optical light output peak at 200-500 nm wavelength range; and third optional output peak at 700-1000 nm wavelength range. It can be used for therapeutic, photosynthesis and photomorphogenetic applications.

27 Claims, 2 Drawing Sheets

(51) Int. Cl.
*A01G 7/04* (2006.01)
*H01L 25/075* (2006.01)
*H01L 33/50* (2010.01)

(52) U.S. Cl.
CPC ................ *H01L2924/00014* (2013.01); *H01L 2924/01322* (2013.01)

(56) References Cited

U.S. PATENT DOCUMENTS

2007/0223219 A1  9/2007  Medendorp, Jr. et al.
2010/0259190 A1  10/2010  Aikala

\* cited by examiner

WIDE SPECTRUM LED COMPONENTS

BACKGROUND OF THE INVENTION

1. Field of the Invention

The present invention relates to light emitting diode (LED) components and the uses thereof. In particular, the invention concerns LED components with a wide light spectrum and having a specific peak intensity. The use of the present LED components for therapeutic, photosynthesis or photomorphogenetic use, such as in skin, muscle, wound treatments as well as activate other various receptors and chemical and physical reactions in living organisms, is also disclosed. The LED components can be also used for a plant cultivation process such as greenhouse growing or crops' seedlings growth.

2. Description of Related Art

The plants, crops, animals, humans are proven to benefits for certain parts of UV, visible and near infrared (NIR) spectrum. Various chemical substances may absorb the energy of emitted spectrum and use the energy in photochemical, chemical reaction or otherwise physically active cell activity. These reactions are well known in photosynthesis process in plants. However, it is also indicated that certain specific spectra can improve wound healing or activate cell growth.

Artificial lighting for plant cultivation is an important factor, which determines the cost and nutritional quality of greenhouse vegetables. Efficiency of greenhouse lighting has been improved by application of high-pressure sodium (HPS) lamps, which emit predominantly yellowred light effectively absorbed by chlorophylls. The improvement is achieved owing to a high overall light yield and the emission spectrum suitable for plant cultivation. However, application of light sources with a spectrum substantially different from the solar one, encounters difficulties owing to sensitivity of plants to the spectral composition of light. Particularly in HPS lamps designed for horticulture applications, the blue component can be enhanced; however, a further purposeful tailoring of the spectrum in the red wavelength region of the HPS lamps has limitations. In principle, the spectrum can be adjusted using different phosphors, but data on the spectrum optimal for particular plants are still scarce and fragmental and cannot be optimized.

Light-emitting diodes (LEDs) present a versatile alternative for artificial greenhouse lighting with numerous advantages. In comparison with conventional HPS and fluorescent lamps, LEDs are an energy-efficient, environmentally friendly and longevous source of light. Assembling of LEDs, which are already available in the entire relevant spectral range from near infrared (IR) to near ultraviolet (UV), enables one to tailor the spectrum for optimal growth. Particularly the spectra in the red and far-red regions are essential for successful and efficient plant cultivation typically described as 660 nm region wavelengths contributing most for the photosynthesis and 730 nm region wavelengths contributing most for photomorphogenesis in plants. These types of spectra can be obtained by direct electroluminescence from AlGaAs or AlInGaP semiconductor LEDs or using blue emitting high power (HP) LED which blue light is then converted to RED wavelength with phosphors materials.

The application of light therapy with LEDs will significantly improve the medical care that is available to astronauts on long-term space missions based on NASA experiments. LEDs stimulate the basic energy processes in the mitochondria (energy compartments) of each cell, particularly when near-infrared light is used to activate the color sensitive chemicals (chromophores, cytochrome systems) inside. Proposed Optimal LED wavelengths include 680, 730 and 880 nm and those have improved the healing of wounds in laboratory animals. Furthermore, DNA synthesis in fibroblasts and muscle cells has been quintupled using NASA LED light alone, in a single application combining 680, 730 and 880 nm each at 4 Joules per centimeter squared. The light is absorbed by mitochondria where it stimulates energy metabolism in muscle and bone, as well as skin and subcutaneous tissue. Also lasers provide low energy stimulation of tissues which results in increased cellular activity during wound healing including increased fibroblast proliferation, growth factor synthesis, collagen production and angiogenesis. Lasers, however, have some inherent characteristics that make their use in a clinical setting problematic, such as limitations in wavelength capabilities and beam width. The combined wavelengths of light optimal for wound healing cannot be efficiently produced, and the size of wounds that may be treated by lasers is limited. Light-emitting diodes (LEDs) offer an effective alternative to lasers with human and animal populations include treatment of serious burns, crush injuries, non-healing fractures, muscle and bone atrophy, traumatic ischemic wounds, radiation tissue damage, compromised skin grafts, and tissue regeneration.

As known in the art, there are several applications that benefit on the availability efficient and correct spectrum red and far red LEDs. However, producing efficient broad band red and far LEDs devices with optimal spectral emission for various forms of light therapy and plant cultivation is still problematic. In particular the problem arises when broad emission spectrum is beneficial and required at red and/or far red wavelength regions. All phosphorescent materials are sensitive for heat and in particularly so the phosphorescent materials that result in long stokes shift emission. Similarly to phosphorescent materials quantum dot nanoparticles particles such as CdSe—ZnS (core-shell) semiconductor crystals can be used for to produce wavelength conversion shorter wavelengths to higher wavelengths. These wavelength conversion materials are also sensitive for thermal quenching. Alternatively the red and far red emission can be produced by using for example AlGaAS semiconductor LEDs, however, it is known by art that typically these devices in order to be efficient result in relatively narrow emission spectrum with narrow less than 50 nm full width of half maximum.

SUMMARY OF THE INNOVATION

Generally, certain embodiments of the present invention address the difficulty of producing high quantum efficiency broad band red/far red emission LED devices.

Furthermore, certain embodiments of the present invention provide an LED component which is capable of being used, for example, for therapy, to aid in cell grow and metabolism activation, photosynthesis, photomorphogenesis and photo coloring with human, animals and plants and being particularly beneficial due to board emission spectrum at red/far red wavelength region.

The spectra of LED devices according to embodiments of the present invention produce a board spectrum at red/far red regions with high efficiency.

An aspect of certain embodiments of the present invention is to provide one or more LED devices having a board spectrum at red/far red regions with high efficiency and having optional board emission spectrum at a wavelength range of 400 to 500 nm.

Further, it is an aspect of certain embodiments of the present innovation to use inorganic phosphor materials for partial or full wavelength conversion of 300-500 nm wavelength range to 600-800 nm wavelength range with low thermal or internal quenching of the conversion efficiency.

It is also an aspect of certain embodiments of the present invention to obtain a LED device by using nano sized semiconductor quantum dot wavelength conversion material with relatively broad particle size distribution resulting in a broad emission peak at red/far red wavelength region.

Furthermore, it is an aspect of certain embodiments of the present invention to provide a LED light source which aids in, for example, cell grow action, photosynthesis, photomorphogenesis and photo coloring with human, animals and plants needs by being capable of sufficiently penetrating at least a portion of the object by providing a broad red/far red emission spectrum and optional a broad blue range emission spectrum with sufficient electro-magnetic radiation intensity.

Aspects of embodiments of the present innovation are based on providing a light emitting diode (LED) component with light emitters, e.g. diodes. Said component is capable of providing a wide light spectrum and having a first peak intensity in the wavelength range of 600-800 nm. The light output spectrum on the 600-800 nm wavelength range has a full width of half maximum in minimum 50 nm.

More specifically, the present LED component is characterized by what is stated in the characterizing part of claim 1.

Uses are characterized by what is stated in claims 22 to 26.

The method of aiding in a photo stimulation process is characterized by what is stated in claim 27.

Considerable advantages are obtained by the present technology. Thus, the output light of an LED component as herein disclosed is beneficial for, for example therapeutic, photosynthesis or photomorphogenetic use such as in skin, muscle, wound treatments as well as activate other various receptors and chemical and physical reactions in living organisms.

The LED component can, for example, also be used within a plant cultivation process, such as greenhouse growing or crops' seedlings growth.

An LED component according to certain embodiments of the present invention can be assembled with a plurality of the same or other output spectra LEDs. The LED component may also comprise, consist of, or consist essentially of, several types of semiconductor electro-luminescent emission sources, and light emission output may comprise, consist of or consist essentially of a combination of phosphorescent and electro-luminescent light emissions in the wavelength range from 200 to 1000 nm.

Next, the innovation will be described in more closely with the aid of a detailed description and a number of non-limiting working examples. Reference is made to the accompanying drawings.

DETAILED DESCRIPTION OF PREFERRED EMBODIMENTS

Definitions

In the present context, the terms "photoluminescence", "luminescence", "phosphorescence" and "fluorescence", stand for, generally, emission of light generated by material or materials absorbing photons then re-emitting light at different wavelength such as fluorescence or phosphorescence. Photoluminescence can be generated at least by phosphors, quantum dots, photo luminescent dyes, but the concept is limited to these.

"Electroluminescence" denotes, generally, emission of light as a result of radiative recombination of electrons and holes in a material, typically usually a semiconductor material.

The present innovation provides an optimal emission spectrum LED component for living cells activation know for example as therapeutic, cell grow and metabolism activation, photosynthesis, photomorphogenesis due to a broad emission peak at 600 to 800 nm wavelength range. Human, animal and plant cells absorb efficiently in 600 to 800 nm wavelength range however different cells still have more selective yet relatively broad absorption bands in the given wavelength region. Due to the board emission peak of the LED component described by the innovation, the light energy is more efficiently transferred into the object. The innovation provides a LED component design to facilitate efficient generation of a broad emission peak at 600 to 800 nm wavelength range. Finally the innovation describes a utilization of semiconductor quantum dots and nanoparticulate phosphor materials to obtain a preferable board emission peak at 600 to 800 nm wavelength range.

The LED device with a wavelength converter material of the partial- or complete-conversion of the LED's electroluminescence may contain a supplementary phosphor which absorbs a portion of the emission with a wavelength shorter than 500 nm and emits red/far-red light in the spectral range of 600 to 800 nm, which meets the photosynthetic and photomorphogenetic needs of plants. Such a phosphor can be an oxide, halooxide, chalcogenide, nitride or oxynitride compound activated by ions of divalent or tetravalent manganese, divalent or trivalent europium, trivalent bismuth, or divalent tin.

For example, the supplementary red component can be generated in inorganic phosphors, such as but not limited to: $Mg_2SiO_4:Mn^{2+}$; $Mg_4(F)GeO_6:Mn^{2+}$; $(Mg,Zn)_3(PO)_4:Mn^{2+}$; $Y_3Al_5O_{12}$ $Mn^{430}$; $(Ca,Sr,Ba)_2Si_5N_8:Eu^{2+}$; $Sr_2Si_4AlON_7IEu^{2+}$; $MgO—MgF_2—GeO_2$ $Eu^{2+}$; $Y_2O_2S:Eu^{3+},Bi^{3+}$; $YVO_4:Eu^{3+},Bi^{3+}$; $Y_2O_3:Eu^{3+},Bi^{3+}$; $SrY_2S_4$ $Eu^{2+}$ $SrS:Eu^{2+}$; $MgSr_5(PO)_4:Sn^{2+}$; $(Ca):SiN_2:Ce^{2+}$; $(Ca,Sr)SiN_2:Eu^{2+}$; $(Ca,Ba)SiN_2,AlO:Eu^{2+}$; $(Ca,Sr,Ba)_2Si5N_8:Eu^{2+}$; $Gd_3Ga_5OCr^{3+}$; $(Ca,Sr,Ba)_2Si5N_8:Eu^{2+}$ and $Gd_3Ga_{50}12:Cr^{3+}$.

However, as known by the art all wavelength conversion materials are subject for thermal quenching in some degree and in particularly long stokes shift phosphor wavelength conversion materials are susceptible for thermal quenching of conversion efficiency. Here in particular long stokes shift is considered to be more than 150 nm wavelength shift from a blue emission peak emission to red or far red wavelength region. As with common LED devices the phosphor material is located to a close proximity to the semiconductor diode such InGaN as a chip. Therefore the phosphorous material is subject to heat produced by the semiconductor chip and resulting in non-radiative recombination. Phosphorous materials are also subject for self-heating meaning that part of the emission from the semiconductor diode chip is absorbed by the phosphor and transformed into heat in the material. Self-heating is further increased then phosphor particles are densely packed particles and are causing a lot of scattering of the diode chip emitted light and thus part of the scattered light energy coverts to heat, which lowers the conversion efficiency. In order to avoid thermal quenching and self-heating quenching derived conversion efficiency decrease in LED devices a novel LED component was designed. In particular the new design addresses use of light conversion materials with wavelength stokes shift more than 150 nm.

The new design comprises a plurality semiconductor diode chips with emission characteristics between 200 and 500 nm and more typically between 350 and 500 nm in a plastic leaded chip carrier. The carrier was designed to comprise or consist of an anode, a cathode and a through package metallic heat sink slug. The PLCC consists of a cavity wherein the cathode, the anode and the heat sink are located. The semiconductor diode chips are bonded to the metallic slug heat sink with a thermally conductive adhesive or via eutectic bonding and the anode and cathode electrical bonds are with gold or copper wire bonds. According to this innovation the diodes are preferably positioned from each other at least the chip's own width, e.g., 10 mil wide chip's edge to edge to distance is at least 10 mil or more. According to the invention it is also beneficial that the semiconductor diode chips are not centrally aligned but the innovation is not limited to this central alignment rule. The semiconductor diode chips are then coated with silicone encapsulate containing wavelength conversion material. The concentration of the wavelength conversion material in the encapsulant varies depending on the conversion material type and how much of the semiconductor diode light emission is desirable to be converted from shorter to longer wavelength.

According to the innovation, a LED device was constructed with a PLCC cavity surface area of approximately 67 square millimeters and depth of the cavity is 0.8 mm resulting in an approximate volume for the cavity of 54 cubic millimeters. Into the cavity 24 InGaN semiconductor diodes were bonded to a heat sink and wire bonded to the electrical anode and cathode connections.

Figure 1:
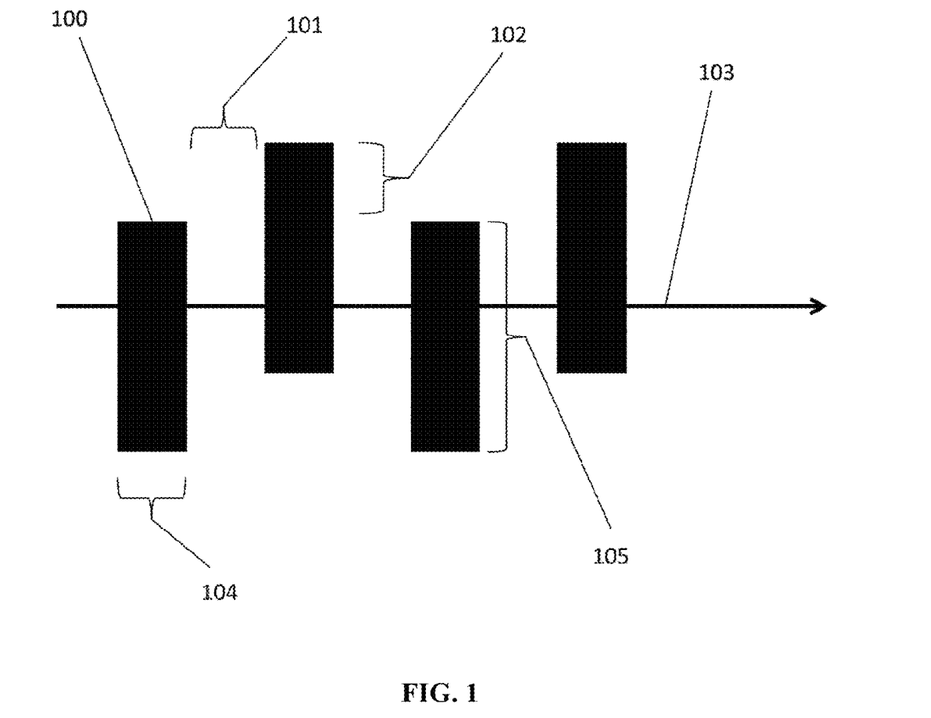
FIG. 1 presents a top view of a plastic leaded chip carrier (PLCC) based LED component arrangement.

FIG. 1 gives a schematic depiction of a PLCC based LED component arrangement, wherein 100 is a light emissive semiconductor diode, 101 is the distance between diodes on the central line of the package, 102 is horizontal de-positioning of adjacent diodes on the central line, 103 is the central line on the PLCC package, 104 is the width of the semiconductor diode chip and 105 is the height of the semiconductor diode chip.

The width 104 of the semiconductor diode chip 100 is 10 mil and therefore the edge to edge distance 101 to next diode is 10 mil or more. The center line 103 of the diodes is also arranged accordingly to FIG. 1 wherein each adjacent diode are de-positioned from the center line. This LED component design is also preferable for side emitting semiconductor light emitting devices due to their low operating temperature compared to high brightness surface emitting devices and also present lower cost of materials.

Figure 2:
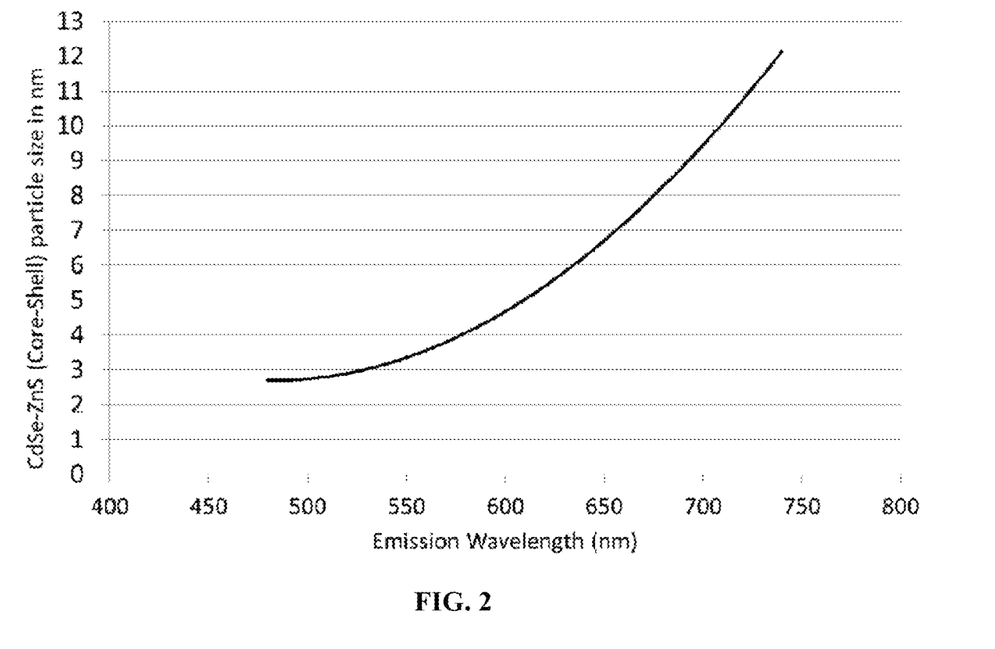
FIG. 2 exhibits typical relationship of CdSe—ZnSe (core-shell) quantum dot size in function of light emission wavelength.

According this innovation it is also possible to obtain a preferable broad wavelength spectrum by using semiconductor quantum dot materials as a light conversion material from shorter wavelength (200-500 nm) to higher wavelength (600-800 nm). The semiconductor quantum dot materials are also susceptible for thermal quenching in the wavelength conversion efficiency. Therefore the LED component arrangement according to the innovation and accordingly to FIG. 1 is preferable for an electroluminescent diode with emission wavelength is below 500 nm and the emission wavelength is to be converted to 600-800 nm wavelength range. CdSe—ZnS (core-shell) quantum dot nanoparticles for example are applicable for the purpose of the invention to have 300-500 nm wavelength electroluminescence conversion to 600-800 nm wavelength range. In FIG. 2 CdSe—SnS (core-shell) particle size relation to emission wavelength is shown. According to the innovation it is also beneficial to use a broad distribution range of quantum dots as wavelength light conversion material and therefore obtain emission spectrum with full width at full maximum broader than 50 nm at 600-800 nm wavelength range.

According the innovation it is also preferable to use nanoparticulate light conversion phosphor materials in applications of long stokes shift wavelength conversion. Due to smaller particle size the quantity of the wavelength converter can be reduced per volume to achieve sufficient wavelength conversion from 300-500 nm wavelength region to 600-800 nm wavelength region. Again, higher conversion efficiency can be achieved when compared to conventional LED packages.

According to the innovation the PLCC package can be also designed so that the component contains at least two types of light emissive semiconductor diode chips for example at least one InGaN diode chip and at least one AlGaAs or AlGaInP diode chip. The innovation is not limited to these semiconductor diode types. The semiconductor diode chips can be electrically connected in serial and/or parallel. It is preferred according to the invention that the first diode emits at a range of 300 to 500 and the second diode emits at a wavelength range of 600 to 1000 nm. More specifically the second diode's emission peak is in a wavelength range of 640 to 700 nm, 720 to 740 nm or 870 to 900 nm. According to the innovation there can be also three different types of LEDs with all having different characteristic spectral emission peaks.

Conventionally used single semiconductor chip (or 2 or 3 semiconductor chip's) containing high brightness LED's produce very point source type emission from the LED package. This high brightness point source emission can be "diffused" by using specially designed optics in connection with the LED or using specially designed light guiding/diffusing sheets/films in close proximity of the LED package. The use of complicated optics and light management optics/sheet/films impact on the cost of the final LED lamp and furthermore reduce efficiency of the LED package/lamp due to losses at the optical interfaces. It is important for LED lamp that are used for the therapeutic, cell grow action, metabolism activation and photomorphogenesis purposes especially with human and animals that there is sufficient intensity uniformity in terms of radiation intensity at the treated surface area. In some cases the point source like treatment light can be preferred but in general uniform distribution of light is preferred. In the current invention we describe the usage of multi semiconductor chip high brightness LED package (for example 24 individual semiconductor chips in one single LED package), which does not suffer from the above mentioned "single point source" issues. High intensity uniformity can be achieved without using any optics or potentially using very simple diffuser sheet in connection with the final LED lamp. This results in an excellent approach to produce LED light sources which produce uniform light intensity distribution even from very close proximity illumination/treatment distances.

As described before the multi semiconductor chip high brightness LED package can be constructed of several individual semiconductor chips. Depending of the architecture of the LED package the individual chips can be connected in series or parallel or both within one individual LED package. Furthermore, it is possible to use one or several type individual semiconductor chips to construct the multi chip LED packages. These individual chips may have also different emission wavelengths within the one multi chip LED package. In some cases it might be preferable to use also zehner diodes or other control mechanisms within one LED package to take into account possible failure of single semiconductor chips in the LED package.

The above mentioned LED packages are then used in the actual final LED lamp fixtures. In one LED lamp fixture there can be one or more LED packages/light engines used. Within the LED lamp these individual packages can be connected in series or parallel depending on the desired electrical properties (voltage, current and power) of the final LED lamp. Again, it might be preferable to use zehner diodes or other control mechanisms within LED lamp between the individual LED packages to take into account possible failure of single LED package in the LED lamp.

The LED lamp fixtures can be designed to have different forms. In general can be identified so called general room lighting providing LED lamps and then closer proximity used LED lamps. The general lighting type of LED lamps fixture can be tube light lamp fixtures (used similar way to the fluorescent tubes) and panel lights (assembled to the ceiling of the room) and also block lights like example high pressure sodium lamps used in greenhouse cultivation (assembled to high altitude in greenhouse). Closer proximity LED lamps can be example face treatment/illumination lamps and "treatment pens", which are both used in very close proximity of face or skin. The body of the LED lamp fixture needs to be able to function as a heat sink and to be able to efficiently dissipate the heat generated by the LED packages.

In greenhouses the LED lamps can be used either as ceiling installed general lights or used in closer proximity depending on what type of line and what is being grown in the facility.

Also it is possible use the LED lamps in multilayer growth installations and also as inter lights in between plants. Furthermore, it is possible to use the LED lamps in greenhouses where there are no natural light available or natural light is available part of the day. The LED lamps can be used also in farms for example cows and chickens. By the control of the day length and also control of the light spectrum it is possible to effect on the growth and milk production or egg incubation production of cows and chickens, respectively. Also the quality of the light influences example on the composition of the milk. The LED lights can be used also for skincare and wound healing purposes and cancer pain therapy for example horses or humans, but not limited to these. Furthermore, the LED light can be used in an artificial egg incubation process or in poultry farming industry as a growth and feeding stimulant.

Based on the above, in one embodiment, the present technology provides a method of aiding in a photo stimulation process comprising the steps of providing a first light output spectrum with at least a first output peak in the wavelength range from 600 to 800 nm, said peak having a full width at half maximum of at least 50 nm; a second optional output peak in the wavelength range from 200 to 500 nm, and a third optional output peak in the wavelength range from 700 to 1000 nm, wherein said first and said second and third optional outputs are provided from an LED component.

The method can be used in aiding a process selected from, e.g., the group of therapeutic, cell grow action, metabolism activation photosynthesis, photomorphogenetic and combinations thereof. The LED components can be any of the ones mentioned above and examined more closely in the working examples.

The following non-limiting examples illustrate the invention.

Example 1

A commercial nitride phosphor with peak emission at 660 nm wavelength range and an average particle size of 15 um was mixed into a two component silicone encapsulant resin using planetary centrifuge to ensure high mixing uniformity. The mixing ratio was 5 w-% of the phosphor material in the silicone resin.

The resin containing phosphor material was dispensed as an encapsulant into a plastic leaded chip carrier (PLCC) consisting 24 units of 10 mil×23 mil InGaN light emitting diodes in the PLCC cavity. The volume of the PLCC cavity and dispensed resin was 54 cubic millimeters. The surface are of the dispensed encapsulant was 67 square millimeters. Immediately after dispense the resin was thermally cured first at 150 deg C. hot plate for 5 min and then 150 deg C. oven for 1 hour resulting in highly uniform distribution of phosphor particles in the PLCC cavity. The light emitting diodes were determined to have electroluminescent emission peak at 450 nm (+/−2.5 nm) wavelength range. All diodes were connected to the anode and cathode of the PLCC and electrically parallel to each other. Each diode was subject for 15 to 20 mA forward current and average forward voltage of 3.0 to 3.2V. Therefore each diode in the PLCC package exhibits approximately 45 mW to 65 mW electrical power consumption and the total power consumption of the 24 diodes LED device is close to 1 W.

The InGaN containing PLCC package with the phosphor containing encapsulant material was connect to a DC voltage power source with forward voltage of 3.1V and current of 350 mA. The device optical emission spectrum was characterized to result in two emission peaks one at 450 nm wavelength range and the second at the 660 nm wavelength range. The 660 nm wavelength range emission peak's full width of half maximum was observed to be approximately 95 nm. The full width at half maximum of the 450 nm wavelength peak was approximately 25 nm. The wavelength peak intensity ratios of the 450 nm and 660 nm peaks were 0.5:1, respectively.

Example 2

A commercial nitride phosphor with peak emission at 660 nm wavelength range and an average particle size of 15 um was mixed into a two component silicone encapsulant resin using planetary centrifuge to ensure high mixing uniformity. The mixing ratio was 10 w-% of the phosphor material in the silicone resin.

The resin containing phosphor material was dispensed as an encapsulant into a plastic leaded chip carrier (PLCC) consisting 24 units of 10 mil×23 mil InGaN light emitting diodes in the PLCC cavity. The volume of the PLCC cavity and dispensed resin was 54 cubic millimeters. The surface are of the dispensed encapsulant was 67 square millimeters. Immediately after dispense the resin was thermally cured first at 150 deg C. hot plate for 5 min and then 150 deg C. oven for 1 hour resulting in highly uniform distribution of phosphor particles in the PLCC cavity. The light emitting diodes were determined to have electroluminescent emission at peak 450 nm (+/−2.5 nm) wavelength range. All diodes were connected to the anode and cathode of the PLCC and electrically parallel to each other. Each diode was subject for 15 to 20 mA forward current and average forward voltage of 3.0 to 3.2V. Therefore each diode in the PLCC package exhibits approximately 45 mW to 65 mW electrical power consumption and the total power consumption of the 24 diodes LED device is close to 1 W.

The InGaN containing PLCC package with the phosphor containing encapsulant material was connect to a DC voltage power source with forward voltage of 3.1V and current of 350 mA. The device optical emission spectrum was characterized to result in two emission peaks one at 450 nm wavelength range and the second at the 660 nm wavelength range. The 660 nm wavelength range emission peak's full width of half maximum was observed to be approximately 95 nm. The full width at half maximum of the 450 nm wavelength peak was approximately 25 nm. The wavelength peak intensity ratios of the 450 nm and 660 nm peaks were ≤0.1:1, respectively.

Example 3

A commercial nitride phosphor with peak emission at 660 nm wavelength range and an average particle size of 15 um was mixed into a two component silicone encapsulant resin using planetary centrifuge to ensure high mixing uniformity. The mixing ratio was 5 w-% of the phosphor material in the silicone resin.

The resin containing phosphor material was dispensed as an encapsulant into a plastic leaded chip carrier (PLCC) consisting 24 units of 10 mil×23 mil InGaN light emitting diodes in the PLCC cavity. The volume of the PLCC cavity and dispensed resin was 54 cubic millimeters. The surface are of the dispensed encapsulant was 67 square millimeters. Immediately after dispense the resin was thermally cured first at 150 deg C. hot plate for 5 min and then 150 deg C. oven for 1 hour resulting in highly uniform distribution of phosphor particles in the PLCC cavity. 10 of the light emitting diodes were determined to have electroluminescent emission at peak 460 nm (+/−2.5 nm) wavelength range, 7 of the light emitting diodes were determined to have electroluminescent emission peak at 445 nm (+/−2.5 nm) wavelength range and 7 of the light emitting diodes were determined to have electroluminescent emission peak at 475 nm (+/−2.5 nm) wavelength range. All diodes were connected to the anode and cathode of the PLCC and electrically parallel to each other. Each diode was subject for 15 to 20 mA forward current and average forward voltage of 3.0 to 3.2V. Therefore each diode in the PLCC package exhibits approximately 45 mW to 65 mW electrical power consumption and the total power consumption of the 24 diodes LED device is close to 1 W.

The InGaN containing PLCC package with the phosphor containing encapsulant material was connect to a DC voltage power source with forward voltage of 3.1 V and current of 350 mA. The device optical emission spectrum was characterized to result in two emission peaks one at 460 nm wavelength range and the second at the 660 nm wavelength range. The 660 nm wavelength range emission peak's full width of half maximum was observed to be approximately 95 nm. The full width at half maximum of the 460 nm wavelength peak was approximately 25 nm. The wavelength peak intensity ratios of the 460 nm and 660 nm peaks were 0.3:1, respectively.

Example 4

Two commercial phosphors with peak emissions at 560 nm and 630 nm wavelength range respectively and an average particle size of 15 um were mixed into a two component silicone encapsulant resin using planetary centrifuge to ensure high mixing uniformity. The mixing ratio was 2.0 w-% and 2.5 w-% of the phosphor material in the silicone resin respectively with 560 nm and 630 nm phosphors.

The resin containing phosphor material was dispensed as an encapsulant into a plastic leaded chip carrier (PLCC) consisting 24 units of 10 mil×23 mil InGaN light emitting diodes in the PLCC cavity. The volume of the PLCC cavity and dispensed resin was 54 cubic millimeters. The surface are of the dispensed encapsulant was 67 square millimeters. Immediately after dispense the resin was thermally cured first at 150 deg C. hot plate for 5 min and then 150 deg C. oven for 1 hour resulting in highly uniform distribution of phosphor particles in the PLCC cavity. 12 of the light emitting diodes were determined to have electroluminescent emission at peak 445 nm (+/−2.5 nm) wavelength range and 12 of the light emitting diodes were determined to have electroluminescent emission peak at 465 nm (+/−2.5 nm) wavelength range. All diodes were connected to the anode and cathode of the PLCC and electrically parallel to each other. Each diode was subject for 15 to 20 mA forward current and average forward voltage of 3.0 to 3.2V. Therefore each diode in the PLCC package exhibits approximately 45 mW to 65 mW electrical power consumption and the total power consumption of the 24 diodes LED device is close to 1 W.

Figure 3:
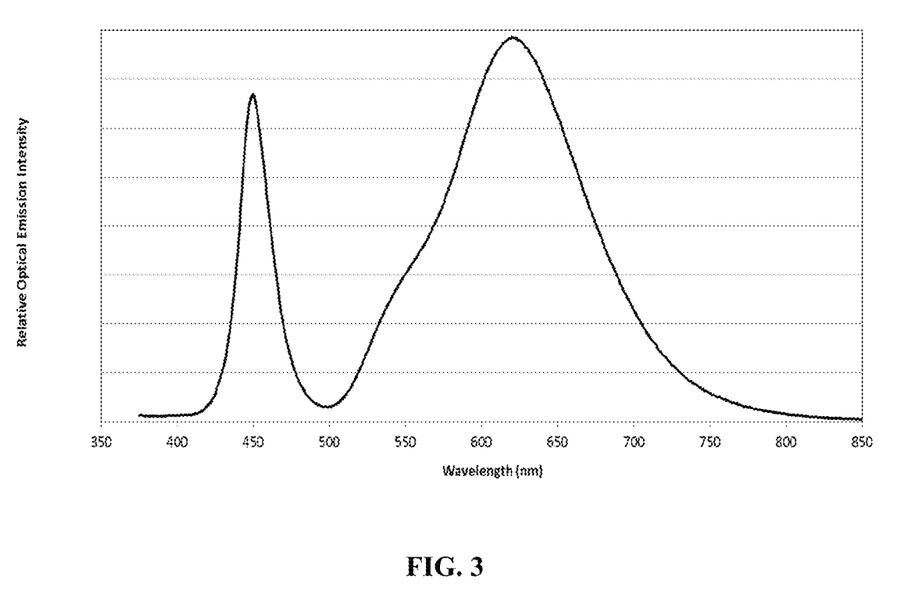
FIG. 3 describes an optical emission of spectrum characterized from the LED panel light explained in Example 4.

The InGaN containing PLCC package with the phosphor containing encapsulant material was connect to a DC voltage power source with forward voltage of 3.1 V and current of 350 mA. The device optical emission spectrum was characterized to result in two emission peaks one at 4 nm wavelength range and the second at the 615 nm wavelength range. The 615 nm wavelength range emission peak's full width of half maximum was observed to be 110 nm. The full width at half maximum of the 455 nm wavelength peak was approximately 30 nm. The wavelength peak intensity ratios of the 465 nm and 615 nm peaks were 0.9:1, respectively. The Spectrum of the device is presented in FIG. 3.

Example 5

A $Ba_{1.8}Sr_{0.2}ZnS_3:Eu_{0.05},Ce_{0.05}$ nano phosphor with peak emission at 680 nm wavelength range and an average particle size of 52 nm was mixed into a two component silicone encapsulant resin using planetary centrifuge to ensure high mixing uniformity. The mixing ratio was 0.5 w-% of the phosphor material in the silicone resin.

The resin containing phosphor material was dispensed as an encapsulant into a plastic leaded chip carrier (PLCC) consisting 24 units of 10 mil×23 mil InGaN light emitting diodes in the PLCC cavity. The volume of the PLCC cavity and dispensed resin was 54 cubic millimeters. The surface are of the dispensed encapsulant was 67 square millimeters. Immediately after dispense the resin was thermally cured first at 150 deg C. hot plate for 5 min and then 150 deg C. oven for 1 hour resulting in highly uniform distribution of phosphor particles in the PLCC cavity. The light emitting diodes were determined to have electroluminescent emission peak at 450 nm (+/−2.5 nm) wavelength range. All diodes were connected to the anode and cathode of the PLCC parallel. Each diode was subject for 15 to 20 mA forward current and average forward voltage of 3.0 to 3.2 V. Therefore each diode in the PLCC package exhibits approximately 45 mW to 65 mW electrical power consumption and the total power consumption of the 24 diodes LED device is close to 1 W.

The InGaN containing PLCC package with the phosphor containing encapsulant material was connect to a DC voltage power source with forward voltage of 3.1V and current of 350 mA. The device optical emission spectrum was characterized to result in two emission peaks one at 450 nm wavelength range and the second at the 680 nm wavelength range. The 680 nm wavelength range emission peak's full width of half maximum was observed to be approximately 150 nm. The full width at half maximum of the 450 nm wavelength peak was approximately 25 nm. The wavelength peak intensity ratios of the 450 nm and 660 nm peaks were 0.5:1, respectively.

Example 6

CdSe—ZnS (core-shell) quantum dot nanoparticles with average particle size of 6.6 nm with approximately +/−0.6 nm particle size distribution were mixed into a two component silicone encapsulant resin using planetary centrifuge to ensure high mixing uniformity. The mixing ratio was 0.2 w-% of nanoparticles in the silicone resin.

The resin containing nanoparticles was dispensed as an encapsulant into a plastic leaded chip carrier (PLCC) consisting 24 units of 10 mil×23 mil InGaN light emitting diodes in the PLCC cavity. The volume of the PLCC cavity and dispensed resin was 54 cubic millimeters. Immediately after dispense the resin was thermally cured first at 150 deg C. hot plate for 5 min and then 150 deg C. oven for 1 hour resulting in highly uniform distribution of phosphor particles in the PLCC cavity. The light emitting diodes were determined to have electroluminescent emission at peak 450 nm (+/−2.5 nm) wavelength range. All diodes were connected to the anode and cathode of the PLCC parallel. Each diode was subject for 15 to 20 mA forward current and average forward voltage of 3.0 to 3.2 V. Therefore each diode in the PLCC package exhibits approximately 45 mW to 65 mW electrical power consumption and the total power consumption of the 24 diodes LED device is close to 1 W.

The InGaN containing PLCC package with nanoparticles containing encapsulant material was connect to a DC voltage power source with forward voltage of 3.1V and current of 350 mA. The device optical emission spectrum was characterized to result in two emission peaks one at 450 nm wavelength range and the second at the 660 nm wavelength range.

The 660 nm wavelength range emission peak's full width of half maximum was observed to be approximately 80 nm. The full width at half maximum of the 450 nm wavelength peak was approximately 25 nm. The peak intensity ratios of the 450 nm and 660 nm peaks were 0.5:1, respectively.

Example 7

CdSe—ZnS (core-shell) quantum dot nanoparticles with average particle size of 6.6 nm with approximately +/−0.5 nm particle size distribution were mixed into a two component silicone encapsulant resin using planetary centrifuge to ensure high mixing uniformity. The mixing ratio was 0.5 w-% of nanoparticles in the silicone resin.

The resin containing nanoparticles was dispensed as an encapsulant into a plastic leaded chip carrier (PLCC) consisting 24 units 10 mil×23 mil InGaN light emitting diodes in the PLCC cavity. The light emitting diodes were determined to have electroluminescent emission peak at 450 nm (+/−2.5 nm) wavelength range. All diodes were connected to the anode and cathode of the PLCC parallel. Each diode was subject for 15 to 20 mA forward current and average forward voltage of 3.0 to 3.2V. Therefore each diode in the PLCC package exhibits approximately 45 mW to 65 mW electrical power consumption and the total power consumption of the 24 diodes LED device is close to 1 W.

The InGaN containing PLCC package with nanoparticles containing encapsulant material was connect to a DC voltage power source with forward voltage of 3.1V and current of 350 mA. The device optical emission spectrum was characterized as resulting in two emission peaks, one in the wavelength range of 450 nm and the second in the wavelength range of 660 nm. The half maximum of the full width of the emission peak at the 660 nm wavelength range was observed to be over 80 nm. Intensity of the 450 nm wavelength range was very low based on spectrum analysis. The peak intensity ratios of the 450 nm and 660 nm peaks were <0.1:1, respectively.

Comparative Example 1

A commercial nitride phosphor with peak emission at 660 nm wavelength range and an average particle size of 15 um was mixed into a two component silicone encapsulant resin using planetary centrifuge to ensure high mixing uniformity. The mixing ratio was 5 w-% of the phosphor material in the silicone resin.

The resin containing phosphor material was dispensed as an encapsulant on a K2 type plastic leaded chip carrier (PLCC) consisting one surface emitting 45 mil×45 mil InGaN light emitting diode on the PLCC top surface mount and also a heat sink slug. The dispensed encapsulant formed a half sphere dome around the diode and covered it uniformly. The volume dome and dispensed resin was 16 cubic millimeters. The radius of the dome was approximately 1.6 millimeters. Immediately after dispense the resin was thermally cured first at 150 deg C. hot plate for 5 min and then 150 deg C. oven for 1 hour resulting in highly uniform distribution of phosphor particles in the dome. After phosphor containing material placement additional clear optical two component silicone was molded on the encapsulant with radius of 2.5 mm to enhance light out coupling from the LED component. The light emitting diode were determined to have electroluminescent emission peak at 450 nm (+/−2.5 nm) wavelength range. The diode was connected to the anode and cathode of the PLCC. The diode was subject for 350 mA forward current and average forward voltage of 3.0 to 3.2V. Therefore the total power consumption of one diode LED device is close to 1 W.

The InGaN containing K2 PLCC package with the phosphor containing encapsulant material was connect to a DC voltage power source with forward voltage of 3.1V and current of 350 mA. The device optical emission spectrum was characterized to result in two emission peaks one at 450 nm wavelength range and the second at the 660 nm wavelength range. The 660 nm wavelength range emission peak's full width of half maximum was observed to be approximately 95 nm. The full width at half maximum of the 450 nm wavelength peak was approximately 20 nm. The wavelength peak intensity ratios of the 450 nm and 660 nm peaks were 0.5:1, respectively.

Comparative Example 2

A commercial nitride phosphor with peak emission at 660 nm wavelength range and an average particle size of 15 um was mixed into a two component silicone encapsulant resin using planetary centrifuge to ensure high mixing uniformity. The mixing ratio was 7 w-% of the phosphor material in the silicone resin.

The resin containing phosphor material was conformally coated as an encapsulant on a silicon based chip carrier consisting one surface emitting 45 mil×45 mil InGaN light emitting diode on the silicon based carrier top surface. The dispensed encapsulant formed a conformal plate on the diode diode and covered it uniformly. The volume dome and dispensed resin was 0.7-0.9 cubic millimeters. Immediately after dispense the resin was thermally cured first at 150 deg C. hot plate for 5 min and then 150 deg C. oven for 1 hour resulting in highly uniform distribution of phosphor particles in the conformal phosphor cap. After phosphor containing material placement additional clear optical two component silicone was molded on the encapsulant with radius of 2.5 mm to enhance light out coupling from the LED component. The light emitting diode were determined to have electroluminescent emission peak at 450 nm (+/−2.5 nm) wavelength range. The diode was connected to the anode and cathode of the PLCC. The diode was subject for 350 mA forward current and average forward voltage of 3.0 to 3.2V. Therefore the total power consumption of one diode LED device is close to 1 W.

The InGaN containing silicon carrier package with the phosphor containing encapsulant material was connect to a DC voltage power source with forward voltage of 3.1V and current of 350 mA. The device optical emission spectrum was characterized to result in two emission peaks one at 450 nm wavelength range and the second at the 660 nm wavelength range. The 660 nm wavelength range emission peak's full width at half maximum was observed to be approximately 95 nm. The full width of half maximum of the 450 nm wavelength peak was approximately 20 nm. The wavelength peak intensity ratios of the 450 nm and 660 nm peaks were 0.5:1, respectively.

Physical, electrical and optical properties parameters are summarized for the examples of the innovation 1 and 3 and comparative examples 1 and 2 in Table 1.

Examples 1 and 3 clearly show higher efficiency to produce spectrum wherein blue light emission energy is partially converted to red and far red wavelength region when compared to the Comparative Examples 1 and 2 This is due to phosphor material proximity to the emissive semiconductor diode. The volume of the light conversion zone, i.e., the dispensed conversion material volume, is larger in the Examples 1 and 3 and resulting in a high average distance for phosphor particles from the semiconductor diode. As the semiconductor diode is generating heat energy in the case of the Examples 1 and 3 the heat is conducted less to the phosphor particles. As a result thermal quenching in phosphor particle is avoided. Also when the phosphor particles are more densely packaged lower radiant flux light output is obtain for the same spectrum. The Comparative Example 2 shows the highest density packaging of the phosphor with the lowest radiant flux output and the lowest conversion efficiency.

surface. The LED's are connected in series on the MCPCB. MCPCB efficiently transfers the heat from the LED to the LED lamp body.) The MCPCB layout design defines the form of the LED lamp body and also the light distribution from the LED lamp together with the LED lamp body design. Typically MCPCB's are used in one plane, but it is also possible to use the MCPCB's in certain angle if certain illumination pattern modification is required.
4. Zehner diodes (each LED has its own Zehner diode to prevent full lamp failure if one individual LED is failing).
5. Heat transfer compound or tape (The heat transfer compound or tape is used between the MCPCB and the lamp body to improve the transfer of the heat from the MCPCB to the body of the lamp).
6. A diffuser sheet (optional). The diffuser sheet is assembled to close proximity to the LED packaged. This can be used for the purpose of making individual LED packages non-visible to the viewer.
7. LED power source and driver. The LED power source and driver can be external units (or unit) to the lamp or they can be integrated inside the LED lamp fixture. When using 15 units of 1 W LED's in series (with driving current of 350 mA, and forward voltage of 3.1V) the power supply voltage needs to be at least 50V-60V and power rating should be at least 20W, supplying constant current at 350 mA.

Short description of the LED lamp assembly:
1. LEDs, zehner diodes and possible connectors are reflow soldered on the MCPCB.
2. This MCPCB is then attached to the LED lamp body. Between the MCPCB and LED lamp body, heat transfer liquid or heattransfer tape is being used. The MCPCB is

TABLE 1

| Example # | Electrical Power | Radiant flux light output | Efficiency (%) | Peaks intensity ratio (Blue:Red) | Peak position/ FWHM | Average phosphor distance to diode |
| --- | --- | --- | --- | --- | --- | --- |
| Example 1 | 1 W | 297 mW | 29.7 | 0.5:1 | 660 nm/95 nm | High |
| Example 3 | 1 W | 330 mW | 33.0 | 0.3:1 | 660 nm/95 nm | High |
| Example 4 | 1 W | 422 mW | 42.2 | 0.9:1 | 615 nm/110 nm | High |
| Comparative 1 | 1 W | 222 mW | 22.2 | 0.5:1 | 660 nm/95 nm | Small |
| Comparative 2 | 1 W | 140 mW | 14.0 | 0.5:1 | 660 nm/95 nm | Very small |

Example 8

General Assembly Method of Use for Light Emitting Diode Light

This example describes fabrication of a LED lamp where 15 individual 1 W PLCC LED packages are being used. The 1 W PLCC LED packages were manufactured according to the Example 1 described above.

The following items will be used to manufacture the LED Panel lamp:
1. 15 pieces of 1 W PLCC LED.
2. Tube lamp body (Aluminium; the body of the lamp is specifically designed to function as a heat sink. The heat sink dissipates the heat generated by LEDs. The individual semiconductor chip junction temperature should be kept below 120 deg C. or preferably below 105 deg C. or even below 90 deg C. This can be achieved by optimized design of the heat sink and layout of the individual LEDs on the LED lamp body).
3. Metal core printed circuit board (MCPCB); (The 15 individual 1 W LEDs are reflow soldered on the MCPCB attached to the LED lamp body by using screws (not fully necessary if heat transfer tape is used).
3. Driver and Power supply are connected to the MCPCB and necessary wiring and grounding of the LED lamp is done in connection to this process.
4. The LED lamp body is equipped with an optional diffusor sheet
5. Finally the LED lamp and all related wiring and connectors are sealed to achieve required usage condition specification. Example typically in case of greenhouse light the requirement is IP65 classification.

Example 9

Blue/Red/Far Red Panel Light

Figure 4:
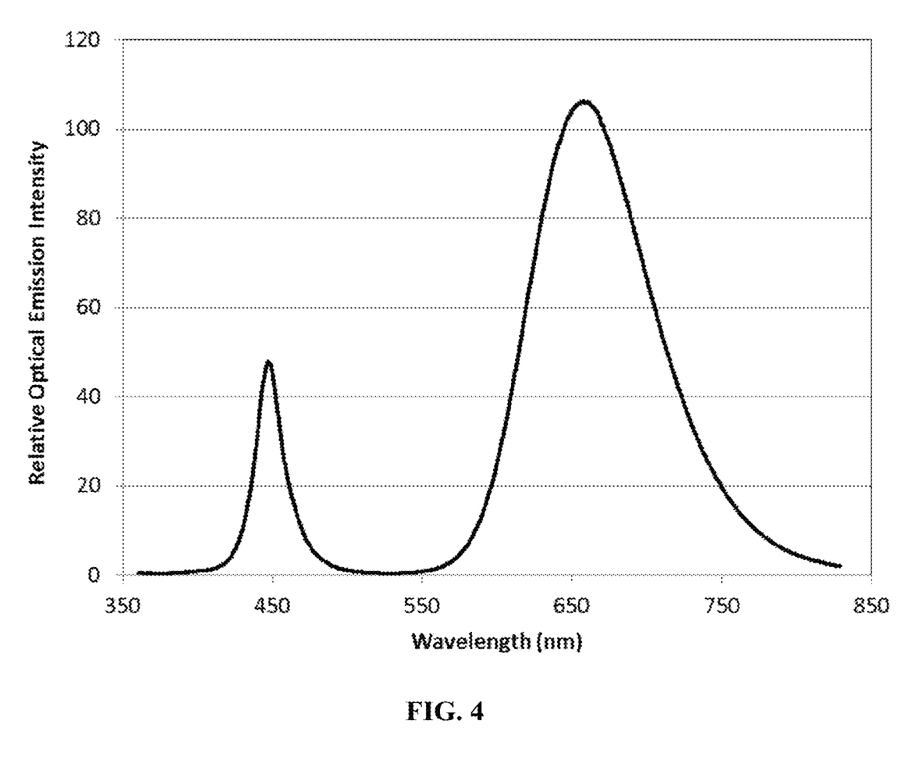
FIG. 4 describes an optical emission of spectrum characterized from the LED panel light explained in Example 9.

The LED component of the Example 1 is used to assemble a panel light for therapeutic, photosynthesis and photomorphogenetic use. The panel light comprises 4 MCPCBs with 12 individual LED components described in the Example 1. The LEDs are soldered to the MCPCB electrically in series. Each MCPCB is 570 mm long. The panel light also comprises a reflector sheet, light guide sheet with single sided reflection pattern and diffuser sheet. Each of the sheets is 580 mm×580 mm in size. Thicknesses of the reflector, light guide and diffuser sheets are 125 micrometer, 6 mm and 250 micrometer, respectively. The sheets are assembled as a stack, the reflector sheet at the top, the light guide in the middle and the reflector at the bottom. The stack of the sheets are framed with anodized aluminum and supported from back with aluminum back plane. The MCPCB are assemble into aluminum frames between the frame and edge of the sheet stack. The LEDs' front surfaces face to the edge the sheet stack. Each 4 MCPCBs are connected in series and then electrically wired to a constant current DC voltage power source. Output current from the power source to the LEDs was set to be 350 mA and the output voltage measured to be 150V. The total power consumption of the panel light including the power source was measured to be 57 watts. The light output spectrum of the light is given in FIG. 4, which comprises two individual emission peaks, one at 450 nm wavelength range and another on 660 nm wavelength range. Due to a broad emission band at 660 nm range the total spectrum provides light at blue, red and far red wavelengths.

Example 10

LED Component Module 1

A commercial nitride phosphor with peak emission at 660 nm wavelength range and an average particle size of 15 um was mixed into a two component silicone encapsulant resin using planetary centrifuge to ensure high mixing uniformity. The mixing ratio was 5 w-% of the phosphor material in the silicone resin.

The resin containing phosphor material was dispensed as an encapsulant on a MCPCB carrier consisting 100 units of 10 mil×23 mil InGaN light emitting diodes and 2 units of 45 mil×45 mil AlGaAs light emitting diodes surrounded with plastic ring to create a dispense cavity. The volume of the cavity and dispensed resin was 254 cubic millimeters. The surface are of the dispensed encapsulant was 254 square millimeters. Immediately after dispense the resin was thermally cured first at 150 deg C. hot plate for 5 min and then 150 deg C. oven for 1 hour resulting in highly uniform distribution of phosphor particles in the PLCC cavity. The light emitting diodes were determined to have electroluminescent emission peak at 450 nm (+/−2.5 nm) wavelength range. 25 of InGaN diodes were connected to the anode and cathode electrically in parallel, 4 similar sets were created with InGaN diodes and these four sets were also connected electrically serial to each other. Two AlGaAs diodes were connect to series to the InGaN diodes. Each InGaN diode was subject for 15 to 20 mA forward current and average forward voltage of 3.0 to 3.2V. Each AlGaAs diode was subject for 350 mA forward current and average forward voltage of 2.1 to 2.2V. The emission wavelength of the AlGaAs diodes was characterized to be 730 nm. The total power consumption of the module was characterized to be 5.9 W when DC electrical parameters for current and voltage were 350 mA and 16.8V.

The LED component module's optical emission spectrum was characterized to result in three emission peaks one at 450 nm wavelength range, the second at the 660 nm wavelength range and third at 730 nm. The 660 nm wavelength range emission peak's full width at half maximum was observed to be approximately 95 nm. The full width at half maximum of the 450 nm wavelength peak was approximately 25 nm. The full width at half maximum of the 730 nm peak was approximately 25 nm, however this is was difficult determine accurately due to partial overlap of 660 nm and 730 nm peaks.

Example 11

LED Component Module 2

A commercial nitride phosphor with peak emission at 660 nm wavelength range and an average particle size of 15 um was mixed into a two component silicone encapsulant resin using planetary centrifuge to ensure high mixing uniformity. The mixing ratio was 5 w-% of the phosphor material in the silicone resin.

The resin containing phosphor material was dispensed as an encapsulant on a MCPCB carrier consisting 100 units of 10 mil×23 mil InGaN light emitting diodes and 2 units of 42 mil×42 mil AlGaInP light emitting diodes surrounded with plastic ring to create a dispense cavity. The volume of the cavity and dispensed resin was 254 cubic millimeters. The surface are of the dispensed encapsulant was 254 square millimeters. Immediately after dispense the resin was thermally cured first at 150 deg C. hot plate for 5 min and then 150 deg C. oven for 1 hour resulting in highly uniform distribution of phosphor particles in the PLCC cavity. The light emitting diodes were determined to have electroluminescent emission peak at 450 nm (+/−2.5 nm) wavelength range. 25 of InGaN diodes were connected to the anode and cathode electrically in parallel, 4 similar sets were created with InGaN diodes and these four sets were also connected electrically serial to each other. Two InGaAs diodes were connect to series to the InGaN diodes. Each InGaN diode was subject for 15 to 20 mA forward current and average forward voltage of 3.0 to 3.2V. Each AlGaInP diode was subject for 350 mA forward current and average forward voltage of 2.1 to 2.2V. The emission wavelength of the AlGaInP diodes was characterized to be 850 nm. The total power consumption of the module was characterized to be 5.9 W when DC electrical parameters for current and voltage were 350 mA and 16.8V.

The LED component module's optical emission spectrum was characterized to result in three emission peaks one at 450 nm wavelength range, the second at the 660 nm wavelength range and third at 850 nm. The 660 nm wavelength range emission peak's full width at half maximum was observed to be approximately 95 nm. The full width at half maximum of the 450 nm wavelength peak was approximately 25 nm. The full width at half maximum of the 850 nm peak was approximately 25 nm.

As described above, there is described herein an LED component comprising at least one light emitter and being capable of providing a light output spectrum with at least a first output peak in the wavelength range from 600 to 800 nm, said peak having a full width at half maximum of at least 50 nm; a second optional output peak in the wavelength range from 200 to 500 nm, and a third optional output peak in the wavelength range from 700 to 1000 nm.

The invention claimed is:
1. An LED component comprising;
  a plurality of electrically connected light emitting diodes, at least a portion of said plurality having a peak wavelength emission between 200-500 nm, and
  an encapsulant material comprising a photo luminescent material and a base material, said encapsulant material at least partially encapsulating said plurality of light emitting diodes,
wherein the LED component has a first light output spectrum with at least a first output peak in the wavelength range from 600 to 800 nm, said peak having a full width at half maximum of at least 50 nm and a second light output peak corresponding to said portion of the plurality of light emitting diodes, and the second light output peak having a peak wavelength emission between 200 and 500 nm is obtained with at least two emissive semiconductor chips having emissive output wavelength peaks at least 5 nm apart from each other.

2. An LED component according to claim 1, wherein the density of the photo luminescent material portion of the encapsulant material and the average distance of photo luminescent partials from the plurality of light emitting diodes are such that the LED component has an efficiency of greater than 23%.

3. The LED component as claimed in claim 1, wherein the first output peak comprises at least one or more photo luminescent material characteristic emissions, photo luminescent emission output peak having a full width at half maximum of at least 100 nm or higher.

4. The LED component as claimed in claim 1, wherein the full width at half maximum is less than 50 nm for the second optical light output peak at the wavelength range 200 to 500 nm.

5. The LED component as claimed in claim 1, wherein the output emission in the wavelength range from 600 to 800 nm is photo luminescent emission and the optional output emissions in the wavelength ranges of 200 to 500 nm and 700 to 1000 nm, respectively, are electroluminescent light output emissions.

6. The LED component as claimed in claim 1, wherein optical emission output in wavelength range of 600 to 800 nm comprises or consists of two photo luminescent emission peaks, both with a full width at half maximum of at least 50 nm.

7. The LED component as claimed in claim 1, wherein the second optional light output peak in the wavelength range of 200 to 500 nm is obtained with a plurality of light emissive semiconductor diodes comprising;
   a) at least one diode with a peak wavelength emission below 450 nm;
   b) at least one diode with a peak wavelength emission between 445 and 465 nm; and
   c) at least one diode with a peak wavelength emission above 460 nm.

8. The LED component as claimed in claim 1, comprising at least 10 individual semiconductor components with electro-luminescent emission between 200 and 500 nm.

9. The LED component as claimed in claim 1, comprising a plurality of semiconductor diode chips with emission characteristics between 200 and 500 in a plastic leaded chip carrier.

10. The LED component according to claim 9, wherein the carrier comprises an anode, a cathode and a through package metallic heat sink slug.

11. The LED component according to claim 9, wherein the plastic leaded chip carrier comprises a cavity wherein the cathode, the anode and the heat sink are located.

12. The LED component according to claim 1, comprising a plurality of diodes, at least a portion of which being positioned from each other at a distance amounting to at least the chip's own width.

13. The LED component according to claim 1, comprising a plurality of diodes, said diodes or semiconductor diode chips not being centrally aligned.

14. The LED component according to claim 1, wherein the semiconductor diode chips are coated with a silicone encapsulate containing nano particulate wavelength conversion material.

15. The LED component according to claim 1, comprising a light output spectrum with at least one peak intensity in the wavelength range of 600 to 800 nm with a full width at half maximum at least 50 nm; a second optional optical light output peak in the wavelength range of 200 to 500 nm; and a third optional output peak in the wavelength range of 700 to 1000 nm wavelength range, and at least one emission peak is obtained by quantum dot light conversion material.

16. The LED component according to claim 1, comprising a light output spectrum with at least one peak intensity in the wavelength range of 600 to 800 nm with a full width at half maximum at least 150 nm; a second optional optical light output peak in the wavelength range of 200 to 500 nm; and a third optional output peak in the wavelength range of 700 to 1000 nm wavelength range, and at least one emission peak is obtained by nano particulate photo luminescent light conversion material.

17. The LED component according to claim 1, wherein a plurality of light emitting semiconductor diode chips are electrically parallel connected to each other and at least one additional light emitting semiconductor chip is electrically connected to other diodes in serial.

18. The LED component of the claim 17, wherein electrically parallel connected light emitting diodes are InGaN semiconductors and the serial connected light emitting diode is AlGaAs or AlGaInP semiconductor diode.

19. A LED component comprising at least one light emitter and being capable of providing a light output spectrum with at least a first output peak in the wavelength range from 600 to 800 nm, said peak having a full width at half maximum of at least 50 nm; a second output peak comprising two emissive peaks in the wavelength range from 200 to 500 nm, the two emissive peaks of the second output peak being at least 5 nm apart from each other and a third optional output peak in the wavelength range from 700 to 1000 nm.

20. A method of aiding in a photo stimulation process comprising the steps of providing a first light output spectrum with at least a first output peak in the wavelength range from 600 to 800 nm, said peak having a full width at half maximum of at least 50 nm; a second output peak in the wavelength range from 200 to 500 nm, and a third optional output peak in the wavelength range from 700 to 1000 nm, wherein said first and said second and third optional outputs are provided from an LED component, wherein the second output peak is obtained with at least two emissive semiconductor chips and the peak emission wavelengths of the chips are at least 5 nm apart from each other.

21. The method of claim 20, wherein the photo stimulation process is therapeutic, cell grow action, metabolism activation photosynthesis, photomorphogenetic or any combination thereof.

22. The method according to claim 20, wherein the first output peak of the LED component comprises at least one or more photo luminescent material characteristic emissions, wherein the phosphorescent emission output peak has a full width at half maximum of at least 100 nm or higher.

23. The method according to claim 20, wherein the full width at half maximum is less than 50 nm for the second optical light output peak at 200 to 500 nm wavelength range.

24. The method according to claim 20, wherein the output emission in the wavelength range from 600 to 800 nm is photo luminescent emission and the optional output emissions in the wavelength ranges of 200 to 500 nm and 700 to 1000 nm, respectively, are electroluminescent light output emissions.

25. The method according to claim 20, wherein optical emission output in wavelength range of 600 to 800 nm comprises two photo luminescent emission peaks, both with a full width at half maximum of at least 50 nm.

26. The method according to claim 20, wherein the second optional light output peak in the wavelength range of 200-500 nm is obtained with a plurality of light emissive semiconductor diodes comprising;
 at least one diode with a peak wavelength emission below 450 nm;
 at least one diode with a peak wavelength emission between 445 and 465 nm; and
 at least one diode with a peak wavelength emission above 460 nm.

27. The method according to claim 20, comprising a light output spectrum with at least one peak intensity in the wavelength range of 600 to 800 nm with a full width at half maximum at least 50 nm; a second optional optical light output peak in the wavelength range of 200 to 500 nm; and a third optional output peak in the wavelength range of 700 to 1000 nm wavelength range, and at least one emission peak is obtained by quantum dot light conversion material.

* * * * *